(12) United States Patent
Barbeau

(10) Patent No.: US 8,778,892 B2
(45) Date of Patent: Jul. 15, 2014

(54) COMPOUNDS AND METHODS FOR TREATMENT OF SOLID TUMORS

(75) Inventor: Donald L. Barbeau, Evanston, IL (US)

(73) Assignee: B & G Partners, LLC, Evanston, IL (US)

( * ) Notice: Subject to any disclaimer, the term of this patent is extended or adjusted under 35 U.S.C. 154(b) by 1091 days.

(21) Appl. No.: 12/381,914

(22) Filed: Mar. 18, 2009

(65) Prior Publication Data

US 2009/0239820 A1 Sep. 24, 2009

Related U.S. Application Data

(60) Provisional application No. 61/070,264, filed on Mar. 21, 2008.

(51) Int. Cl.
| | | |
|---|---|---|
| *A01N 43/04* | (2006.01) | |
| *A61K 31/70* | (2006.01) | |
| *C07H 1/00* | (2006.01) | |
| *C08B 37/00* | (2006.01) | |
| *A61K 31/715* | (2006.01) | |
| *A61K 31/7042* | (2006.01) | |
| *C07H 5/04* | (2006.01) | |
| *C08B 37/08* | (2006.01) | |

(52) U.S. Cl.
CPC ........... *A61K 31/715* (2013.01); *A61K 31/7042* (2013.01); *C07H 5/04* (2013.01); *C08B 37/0063* (2013.01); *C08B 37/0072* (2013.01)
USPC .............. 514/23; 514/62; 536/1.11; 536/55.2

(58) Field of Classification Search
CPC .............................. A61K 31/7042; C07H 5/04
USPC ............................. 514/23, 62; 536/1.11, 55.2
See application file for complete search history.

(56) References Cited

U.S. PATENT DOCUMENTS 6,699,848 B1 * 3/2004 Barbeau ........................ 514/54
2004/0142880 A1 * 7/2004 Barbeau ........................ 514/23

OTHER PUBLICATIONS

Hoffman, B.B. "Therapy of Hypertension" in Goodman and Gilman's The Pharmacological Basis of Therapeutics. Edited by Joel G. Hardman and Lee E. Limbird, published by The McGraw-Hill Companies, Inc., 2006, p. 845-868.*
Kur'yanov, V.O., Chirva, V.Ya., Zemlyakov, A.E. (1989) Synthesis of uronoyldipeptide derivatives of N-acetylglucosamine and of N-acetylmuramoyldipeptide. Chemistry of Natural Compounds, vol. 24, No. 6, p. 725-728. Translated from Khimiya Prirodynkh Soedinenii (1988), No. 6, p. 850-855.*
Ansel, H.C., Allen, Jr., L.V., Popovich, N.G. (1999) Pharmaceutical Dosage Forms and Drug Delivery Systems, published by Lippincott Williams & Wilkins, p. 120-128.*
J. Druey and A. Marxer, "Hypotensive Hydrazinophthalazines and Related Compounds," 1 J. Med. & Pharm. Chem. 1-21 (1959).

* cited by examiner

*Primary Examiner* — Scarlett Goon

(57) ABSTRACT

The present invention relates to pharmaceutical compositions containing targetable bioconjugates of hydralazine, a direct vasodilating agent previously shown to decrease tumor blood flow, oxygenation and interstitial fluid pressure in solid tumors. These bioconjugates are hydralazine prodrugs that contain hydralazine conjugated to biocompatible carrier molecules which specifically bind to sites that are expressed on a diverse variety of tumor cell types. These hydralazine prodrugs are preferably conjugated through an acid-labile hydrazone link that is designed to be stable in plasma and release hydralazine through acid-catalyzed hydrolysis in the acidic environment of the target tumor. Because these prodrugs are stable at physiological pH and in plasma, they are devoid of systemic vasoactive activity; however, they are acid-labile conjugates that can be hydrolyzed upon reaching the more acid environment of the tumor where the vasoactive activity of hydralazine is restored. These prodrugs selectively bind to tumor-specific receptors on tumor cells, and are degraded in the acidic tumor cell environment or the acidic lysosomal compartments after being internalized into the cell.

4 Claims, No Drawings

COMPOUNDS AND METHODS FOR TREATMENT OF SOLID TUMORS

CROSS-REFERENCE TO RELATED APPLICATIONS

This patent application claims the benefit of prior filed provisional application No. 61/070,264 filed Mar. 21, 2008, titled Compounds and Methods for Adjunctive Treatment of Solid Tumors, which is hereby incorporated by reference in its entirety.

BACKGROUND OF THE INVENTION

Solid malignant tumors comprise the vast majority of all human cancers. The non-surgical treatment of patients with malignant solid tumors generally includes ionizing radiation and chemotherapy with cytotoxic chemotherapeutic agents, both of which are affected by the oxygenation status of the tumor. It is well established that oxygen is rapidly metabolized by tumor cells and has limited diffusion distance from vasculature in tissues. As tumors enlarge, their central area has deficient blood supply which results in hypoxic and necrotic tissues. As a whole, tumors comprise well-oxygenated, hypoxic and anoxic areas that respond differently to non-surgical therapeutic treatment. Radiation therapy does not effectively destroy hypoxic areas in tumors unless the radiation dose is increased several-fold above the dose necessary to destroy well-oxygenated areas of the same tumor. Chemotherapeutic agents differentiate between their toxicity toward subpopulations of well-oxygenated and hypoxic tumor sites. We propose that the modulation of the oxygenation and blood perfusion of tumors represents an opportunity to control the effectiveness of existing therapeutic chemotherapies with known safety and efficacy as cytotoxins. Studies have shown that the effectiveness of ionizing radiation and cytotoxic chemotherapeutic agents toward hypoxic solid tumors can be enhanced by modulating the blood flow and oxygenation of the tumors. Studies have shown that the effectiveness of certain cytotoxic chemotherapeutic agents toward hypoxic solid tumors can be enhanced by reducing the blood flow and oxygenation of the tumors.

Vasoactive drugs such as nitroprusside, hydralazine, arginine, and nitroglycerine can selectively reduce tumor blood flow and increase the percent of hypoxic areas in experimental tumors. Hydralazine, nicotinamide, epinephrine, norepinephrine, and nitroglycerin have also been reported to reduce the interstitial fluid pressure (IFP) in tumors. By promoting hypoxia in the tumor, the cytotoxicity of chemotherapeutic agents which are active in hypoxic conditions is enhanced. Unfortunately vasoactive drugs that are therapeutically effective in reducing tumor blood flow in patients are antihypertensive agents that would likely cause hypotension or other side-effects in normotensive patients when present in therapeutically effective plasma concentrations. There is a need for therapeutic compositions that mask the vasoactive properties of these antihypertensive agents in the systemic circulation, which target and deliver these "inactive" vasoactive agents to tumors where they can be "activated" and that provide therapy useful in the treatment of solid tumors with a hypoxic cytotoxic chemotherapeutic agent, radiotherapy or hyperthermia.

It is an object of the present invention to provide a method for treating a subject having a solid tumor comprising administering to the subject a tumor-targeted hydralazine conjugate in an amount effective in modulating tumor blood flow, oxygenation or interstitial fluid pressure.

It is an another object of the present invention to provide a method of enhancing the therapeutic efficacy of cytotoxic chemotherapeutic agents with co-administration of tumor-targeted hydralazine conjugates that selectively reduce blood flow and oxygenation of tumors in a subject having a solid tumor.

It is another object of the present invention to provide a method for treating a subject having a solid tumor comprising administering a chemotherapeutic agent in combination with a tumor-targeted hydralazine conjugate in an amount effective in decreasing tumor blood flow, oxygenation and interstitial fluid pressure.

It is another object of the present invention to provide a method for treating a subject having a solid tumor comprising administering a tumor-targeted hydralazine conjugate in an amount effective in modulating tumor blood flow, oxygenation and interstitial fluid pressure during radiological therapy.

It is another object of the present invention to provide a method for treating a subject having a solid tumor comprising administering a tumor-targeted hydralazine conjugate in an amount effective in decreasing tumor blood flow, oxygenation and interstitial fluid pressure during hyperthermia therapy.

It is another object of the present invention to provide compounds and a method for treating a subject having a tumor comprising administering a tumor-targeted hydralazine conjugate in an amount effective in modulating the inactivation of tumor suppression genes.

BRIEF SUMMARY OF THE INVENTION

The present invention relates to pharmaceutical compositions containing targetable bioconjugates of hydralazine, a direct vasodilating agent previously shown to decrease tumor blood flow, oxygenation and interstitial fluid pressure in solid tumors. These bioconjugates are hydralazine prodrugs having the formula

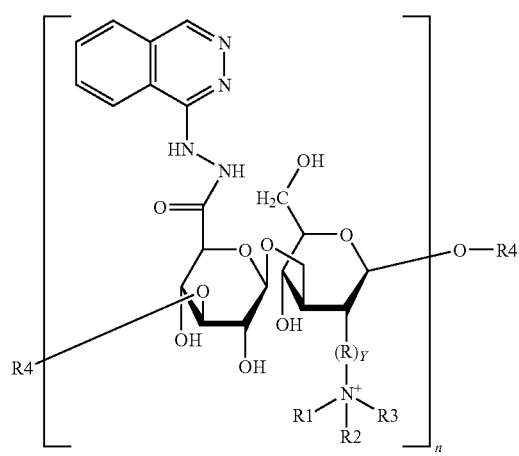

where R is an alkylene, Y=0 or 1, $R_1$, $R_2$ and $R_3$ are independently hydrogen, alkyl, aryl, aralkyl and cycloalkyl, $R_4$ is independently hydrogen or lower alkyl, n is an integer from 1 to about 6 and a pharmaceutically acceptable salt thereof.

DETAILED DESCRIPTION OF THE INVENTION

In accordance with the present invention, the hydralazine bioconjugates comprise hydralazine or a derivative thereof attached to saccharides having a molecular weight less than about 2,000 Daltons, including both monosaccharides and oligosaccharides. In accordance with a preferred embodiment of the present invention, the drug conjugates comprise a pharmacologically active agent (drug residue) covalently attached to water-soluble monosaccharides and oligosaccharides. In accordance with another aspect of the present invention, hydralazine is covalently attached to oligosaccharides having from 2 to about 10 glycoside residues. In a preferred embodiment of the present invention, oligosaccharides include those having from 3 to about 8 glycoside residues.

Unless otherwise specifically identified or claimed for preferred embodiments, the following general definitions are used in accordance with the present invention.

In accordance with the present invention, the term drug residue, hydralazine residue, residue of a pharmacologically active compound or like terms refers to that portion of the conjugated compound which upon release from the saccharide conjugate forms a compound that exhibits the pharmacological activity of the compound.

In accordance with the present invention, the term targetable refers to the recognition of a target and delivery of a drug to that target by the conjugates; however, no internalization of the drug or drug conjugate is inferred. Examples of targets in accordance with the present invention include, without limitation, tumors and the hypoxic regions surrounding those tumors in which the conjugates accumulate.

In accordance with the present invention, the term modulate refers to a change in the parameter measured, such that modulate can mean either an increase or decrease.

In accordance with the present invention, the term alkyl refers to a branched or straight chain acyclic alkyl group comprising one to about ten carbon atoms. In accordance with the present invention, the term lower alkyl refers to a branched or straight chain acyclic alkyl group comprising one to about six carbon atoms.

In accordance with the present invention, cycloalkyl refers to a saturated or unsaturated cyclic hydrocarbon comprising from about 3 to about 8 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. In accordance with the present invention, cycloalkyl groups include cyclopropyl, cyclobutyl, cyclopentyl, cyclohexyl, cyclohexenyl, cycloheptyl and the like.

In accordance with the present invention, the term aryl refers to a unsubstituted or substituted monocyclic, bicyclic, carbocyclic or heterocyclic ring system comprising one or two aromatic rings. In accordance with the present invention, aryl groups include phenyl, pyridyl, napthyl, quinoyl, tetrahydronaphthyl, furanyl, indanyl, indenyl, indoyl, and the like.

In accordance with the present invention, the term arylalkyl refers to an aryl radical, attached to an alkyl radical in accordance with the present invention, In accordance with the present invention, disclosed are targetable bioconjugates of hydralazine, a direct vasodilating agent previously shown to modulate tumor blood flow, oxygenation and interstitial fluid pressure in solid tumors. In one embodiment of the present invention these targetable bioconjugates are oligosaccharides having the formula

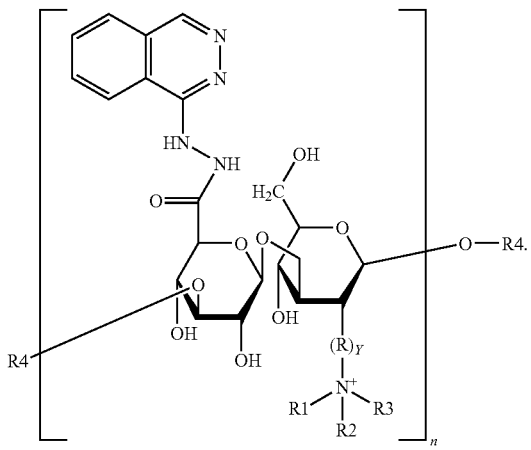

Therapeutic drug oligosaccharide conjugates are described in U.S. Pat. Nos. 6,699,848 and 7,119,079, which are hereby incorporated by reference.

In accordance with the present invention, R is an alkylene containing only carbon atoms or a heteroalkylene containing carbon, nitrogen and oxygen atoms. Examples of heteroalkylenes include —NHC(O)CH$_2$— and —NHC(O)CH$_2$CH$_2$—. In accordance with the present invention, R is an alkylene having from 1 to about 6 carbon atoms. In a preferred embodiment of the present invention, R is a lower alkylene having from 1 to about 3 carbon atoms. In accordance with a more preferred embodiment of the present invention, R is —CH$_2$ or —CH$_2$CH$_2$—. In accordance with the present invention, Y is either 0 or 1. In accordance with a preferred embodiment of the present invention, Y is 0.

In accordance with the present invention, R$_1$, R$_2$ and R$_3$ are independently hydrogen, alkyl, aryl and cycloalkyl. Preferred alkyls are those having from 1 to about 6 carbon atoms including but not limited to methyl, ethyl, propyl, butyl, isobutyl, pentyl and hexyl. More preferably the alkyls contain from 1 to about 3 carbon atoms. In accordance with the present invention, R$_1$, R$_2$ and R$_3$ are each methyl or ethyl. Preferred aryls are those including but not limited to phenyl and pyridinyl, while a preferred aralkyl is benzyl. Preferred cycloalkyls are those having from about 3 to about 6 carbon atoms including but not limited to cyclopropyl, cyclobutyl, cyclopentyl, and cyclohexyl.

In accordance with the present invention, R$_4$ is independently hydrogen or lower alkyl. When R$_4$ is an alkyl, R$_4$ is methyl, ethyl or propyl. Preferably, R$_4$ is hydrogen.

In accordance with this embodiment of the present invention, the oligosaccharides include multiple glycosides such that n is an integer from about 1 to about 6. In a preferred embodiment of the present invention, the conjugates include an oligosaccharide where n is an integer from 2 to about 4. In a more preferred embodiment, the conjugates include an oligosaccharide where n is an integer from 1 to about 2.

Illustrative compounds in accordance with the present invention include hydralazine oligosaccharide conjugates having the formula:

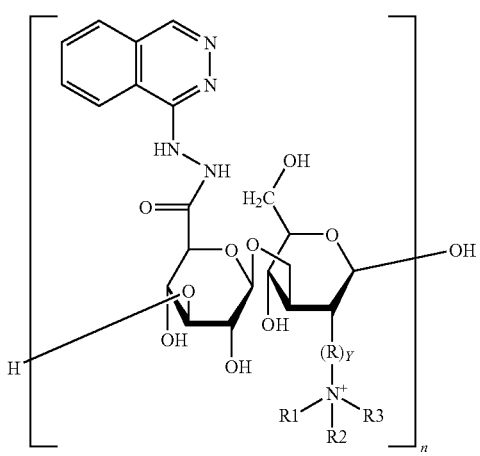

where n is an integer from 1 to about 6. In a preferred embodiment, n is from 1 to about 3.

Illustrative compounds in accordance with another aspect of the present invention include hydralazine oligosaccharide conjugates having the formula:

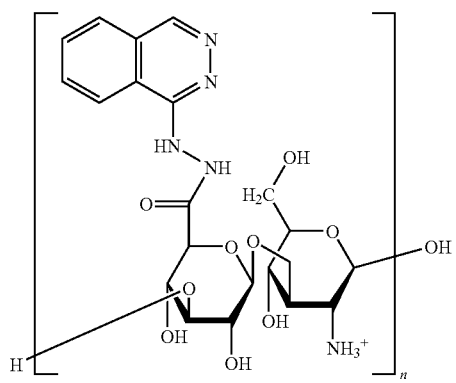

where n is an integer from 1 to about 6. In a preferred embodiment, n is from 1 to about 3.

Illustrative compounds in accordance with another aspect of the present invention include hydralazine oligosaccharide conjugates having the formula:

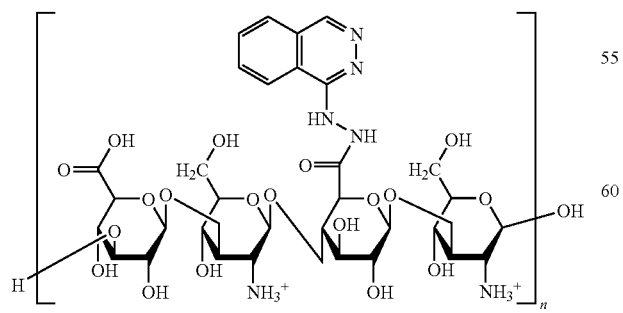

where n is an integer from 1 to about 3.

In accordance with this embodiment of the present invention, it is understood that when n=1 and $R_4$ is hydrogen, preferably the glycosides are hydroxylated as follows:

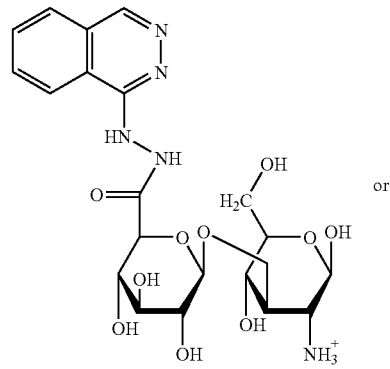

or

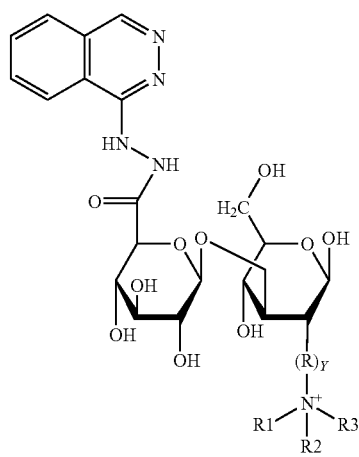

In accordance with the present invention, the oligosaccharide compounds can be chondrosine-based as shown below:

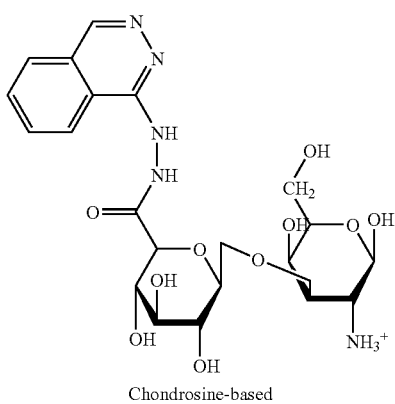

Chondrosine-based or hyalobiuronic acid-based as shown below:

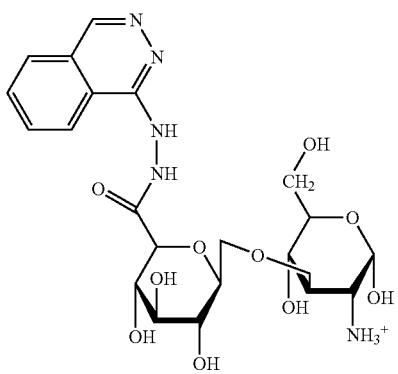

Hyalobiuronic Acid based

In another aspect of the present invention, disclosed are monosaccharide drug conjugates having the formula

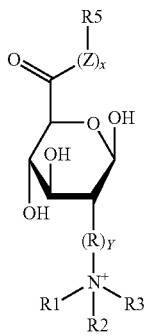

where R is an alkylene, Y=0 or 1, $R_1$, $R_2$ and $R_3$ are independently hydrogen, alkyl, aryl, aralkyl and cycloalkyl, X=0 or 1, Z is oxygen and $R_5$ is a pharmacologically active drug residue or a pharmaceutically acceptable salt thereof. In a preferred embodiment of the present invention, X is 0.

In a more preferred embodiment of this aspect of the present invention, disclosed are compounds having the formula

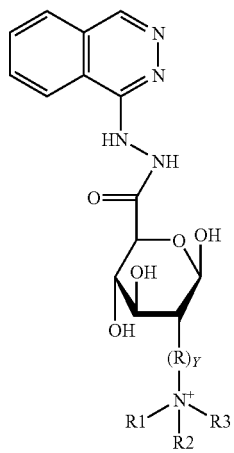

where R is an alkylene, Y=0 or 1, $R_1$, $R_2$ and $R_3$ are independently hydrogen, alkyl, aryl, aralkyl and cycloalkyl and a pharmaceutically acceptable salt thereof. In a preferred embodiment of the present invention, hydralazine is conjugated to 2-amino-D-glucuronic acid (CAS No. 50767-834), resulting in a compound having the formula

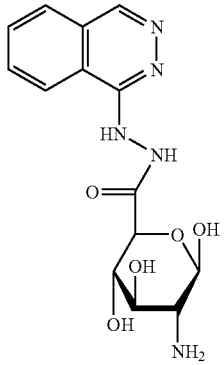

In accordance with one aspect of the present invention, disclosed are drugs conjugates that contain hydralazine conjugated to small hyaluronan-type oligosaccharides which can specifically bind to CD44, a glycoprotein that is over expressed on a tumor cells. Hyaluronic acid, the main component of the extracellular matrix is high-molecular-weight negatively charged biopolymer whose linear structure is created by repeating disaccharide units of N-acetyl-D-glucosamine and D-glucuronic acid. Hyaluronic acid chains, which can reach 2×10(4) kDa in size, are involved in ovulation, embryogenesis, wound repair and regeneration, and protection of epithelial layer integrity. High-molecular-weight hyaluronic acid is broken down under the influence of free radicals and enzymes in the body to smaller fragments that can compete with larger hyaluronic acid polymers for receptors and whose effect on inflammation, immunostimulation and angiogenesis is believed to be closely dependent on its molecular mass. These properties have been demonstrated for tetrasaccharide and pentadisaccharide units of d-glucuronic acid and N-acetyl-d-glucosamine over a wide pH range (68). It has recently been demonstrated that these smaller oligosaccharide fragments of hyaluronic acid, as well as glucosamine analogs themselves, can bind to CD44.

CD44 is a membrane receptor on intact cells that displays a high apparent binding affinity for hyaluronic acid (a $K_d$ of $10^{-9}$ M) most likely due to multivalent interactions with multiple receptors. Hyaluronic acid is a uniformly repetitive, linear glycosaminoglycan composed of 2,000 to about 25,000 disaccharides of glucuronic acid and N-acetylglucosamine having the formula: $[\beta\text{-}1,4\text{-GlcUA-}\beta\text{-}1,3\text{-GlcNac-}]_n$. Binding of hyaluronan to this CD44 is inhibited by small hyaluronan oligosaccharides such as hexasaccharides. On intact cells, other glycosaminoglycans such as chondroitin sulfate or heparan sulfate showed little capacity to compete with hyaluronan for binding. Binding of high molecular weight hyaluronic acid to CD44 is markedly inhibited by hyaluronic acid-derived oligosaccharides of between six and 18 sugars residues, suggesting that a hexamer occupies the binding site.

The hydralazine conjugates of the present invention comprise hydralazine covalently attached to the saccharides through a direct linkage that blocks the pharmacological activity of the active hydralazine molecule in the circulation. Thus, in accordance with the present invention, the antihypertensive activity of hydralazine advantageously is mitigated until it reaches the tumor. Unlike other vasodilators, such as the glyceryl nitrates and isosorbide nitrates, the chemical structure of hydralazine advantageously permits direct conjugation through a pH-labile linkage. The hydralazine-conjugated monosaccharide and oligosaccharides of the present invention are acid-labile hydrazone derivatives that are expected to be stable in plasma, not pharmacologically active at physiological pH and are not endogenously hydrolyzed to parent hydralazine after intravenous administration. This is similar to the immunotargeting of tumors with doxorubicin conjugated to Lewis-Y-related tumor associated antigen monoclonal antibodies, polyethylene glycol or N-(2-hydroxypropyl)methacrylate through hydrazone linkers. These hydrazone conjugates are stable in plasma under physiological conditions (pH 7.4); however, they are acid-labile and are hydrolyzed in the acid environment of the tumor (pH ~5-6) where the doxorubicin is released. In these cases, the hydrazone conjugates are more cytotoxic than those with ester bonds that are hydrolyzed in plasma.

Tumor targeting and cellular uptake of the water-soluble low molecular weight oligosaccharide hydralazine-conjugates of the present invention is determined by a number of conventional techniques described in the scientific literature, including immunofluorescent staining (e.g. FITC or Texas Red) followed by confocal microscopic imaging and flow cytometry/fluorescence activated cell sorting (FACS) using fluorescein labeled conjugates. The effects of our proprietary water-soluble low molecular weight oligosaccharide hydralazine-conjugates on interstitial fluid pressure (IFP), tumor oxygenation, tumor blood flow and cytotoxic activity can easily be determined by a number of conventional techniques described in the scientific literature.

The differential effect of intravenously injected low molecular weight oligosaccharide hydralazine-conjugates on the interstitial fluid pressure (IFP) in various subcutaneous tumors compared with the surrounding normal tissue unaffected can be determine as in Podobnik et al. in Radiol Oncol 34(10: 59-65 (2000) and In Vivo 15: 417-424 (2001). The effect of intravenously injected low molecular weight oligosaccharide hydralazine-conjugates on the oxygenation and blood flow of tumors can be determined with a luminescence-based fiber-optic sensor as described by Jarm et al. in Radiol. Oncol. 35(4): 277-291 (2001); in Oxygen Transport to Tissue XXIII edited by D. Wilson, Kluwer Academic/Plenum Publishers, 2003; and Technology and Health Care 10:363-380 (2002).

Determining the dose and the amount of hydralazine conjugate effective in decreasing tumor blood flow or oxygenation in accordance with the present invention will be apparent to those skilled in the art. The effectiveness of intravenously injected water-soluble low molecular weight oligosaccharide hydralazine-conjugates to decrease tissue perfusion and enhance the anti-tumor activity of hypoxic cytotoxins can be determined as in Horsman et al. in Acta Oncol. 30(5):641-7 (1991); Acta Oncol. 1988; 27(6b):861-2 (1988); and Fisker et al. in Int J Hyperthermia. March-April; 5(2):123-36 (1989).

In accordance with one aspect of the present invention, a method for treating a subject having a solid tumor comprises administering to the subject a water-soluble low molecular weight oligosaccharide hydralazine-conjugate in an amount effective in altering tumor blood flow or oxygenation. In accordance with another aspect of the present invention, a method of enhancing the therapeutic efficacy of cytotoxic chemotherapeutic agents comprises co-administration of water-soluble low molecular weight oligosaccharide hydralazine-conjugate with the cytotoxic chemotherapeutic agent or agents in an amount effective in effective in reducing blood flow and oxygenation of tumors in a subject having a solid tumor. In a preferred embodiment of the present invention, a method for treating a subject having a solid tumor comprises administering a chemotherapeutic agent in combination with a water-soluble low molecular weight oligosaccharide hydralazine-conjugate in an amount effective in decreasing tumor blood flow, oxygenation and interstitial fluid pressure. In accordance with the present invention, a method for treating a subject having a solid tumor comprises administering a water-soluble low molecular weight oligosaccharide hydralazine-conjugate in an amount effective in decreasing tumor blood flow, oxygenation and interstitial fluid pressure during hyperthermia therapy. In each case, the hydralazine conjugates can be administered prior to, during or after the administration of the chemotherapeutic agents or treatment.

In yet another aspect of the present invention, a method for treating a subject having a solid tumor comprises administering a water-soluble low molecular weight oligosaccharide hydralazine-conjugate in an amount effective in enhancing the effectiveness of ionizing radiation by modulating the blood flow and oxygenation of the tumors.

Preferably the therapeutic methods of the invention result in an increase in tumor regression rate (response rate), local tumor control and/or reduction in the frequency of or elimination of growth of metastases in conjunction with systemic chemotherapy.

In accordance with the present invention, the tumor-targeted hydralazine conjugates are administered parenterally, and the preferred route of parenteral administration is intravenous. Preferably the tumor-targeted hydralazine conjugate is prepared in an admixture with a pharmaceutically acceptable salt or carrier. The term "carrier" refers to diluents, excipients and the like for use in preparing admixtures of a pharmaceutical composition. Pharmaceutically acceptable carriers include but are not limited to sterile water, saline, buffered saline, dextrose solution, preferably such physiologically compatible buffers as Hank's or Ringer's solution, physiological saline, a mixture consisting of saline and glucose, and heparinized sodium-citrate-citric acid-dextrose solution and the like. As used herein, the term "pharmaceutically acceptable" means approved by a regulatory agency of the Federal or a state government or listed in the U.S. Pharmacopeia or other generally recognized pharmacopeia for use in animals, and more particularly in humans.

In accordance with the present invention, hydralazine is administered in combination with doxorubicin (adriamycin), mytomycin C, EO9, porfiromycin, melphalan, chlorambucil, AQ4N, CB1954, SN23862, NITP, carboquone, RB-6145, RSU 1164, metronidazole, idarubicin etanidazole, misonidazole, RSU 1069, nitronidazole, tirapazamine (TPZ; SR4233), and NLCQ-1 (4-[3-(2-nitro-1-imidazolyl)-propylamino]-7-chloroquinoline hydrochloride). Generally, the dose of the chemotherapeutic agent will be a dose found to be effective for chemotherapy or lower.

In accordance with the present invention, hydralazine is administered in combination with acidic chemotherapeutic agents whose cytotoxicity is enhanced under acid pH conditions, particularly during hyperthermia. Acidotic cytotoxins include, but are not limited to, cisplatin, analogs of cisplatin, bleomycin, flavone acetic acid and etanidazole. Generally, the dose of the chemotherapeutic agent will be a dose found to be effective for chemotherapy. For the therapy of a hypoxic tumor, the dose of the chemotherapeutic agent may be less than the standard amount administered for chemotherapy or lower.

Chemotherapeutic agents reported to be effective on hypoxic tumors include adriamycin, 3-hydroxy-5-aziridinyl-1-methyl-2(1H-indole-4,7-dione)prop-beta-en-alpha-ol) (a.k.a. EO9), mytomycin C, porfiromycin, melphalan, chlorambucil N-oxide, N-oxide analogue of mitoxantrone (AQ4N), CB1954, SN23862, NITP, carboquone, RB-6145, RSU 1164, metronidazole, etanidazole, idarubicin, misonidazole, RSU 1069, nitronidazole, tirapazamine (TPZ; SR4233), 4-[3-(2-nitro-1-imidazolyl)-propylamino]-7-chloroquinoline and hydrochloride (NLCQ-1, NSC 709257).

Chemotherapeutic agents reported to be effective on oxygenated tumors include procarbazine, streptonigran, actinomycin D, vincristine, cyclophosphamide, BCNU, bleomycin.

In another aspect, the present invention contemplates administration of a tumor-targeted hydralazine conjugate in conjunction with hyperthermia therapy for the treatment of a solid tumor. Hyperthermia therapy refers to use of physical agents, such as but not limited to microwaves, ultrasound, or other heating element for local or regional heating, or radiant heat for total body hyperthermia. Generally, tumor vasculature cannot respond to heat stress as well as normal tissue, and reducing tumor blood flow enhances this effect. Administration of a tumor-targeted hydralazine conjugate further reduces the ability of tumors to responds to heat stress. Furthermore, the present methods can help overcome some of the limitations of hyperthermia therapy that result from the non-uniformity of the temperature within the tumor, particularly regions of the tumor with relatively high blood flow. By reducing tumor blood flow, metabolism in the tumor becomes more anaerobic, resulting in production of lactic acid and a decrease in pH.

In yet another embodiment of the present invention, hydralazine is administered alone to a patient in need of cancer therapy. An example of this embodiment includes the use of hydralazine as a demethylating agent to inactivate tumor suppression genes. DNA methylation is an epigenetic modification of DNA whereby methyl groups are added as part of the covalent structure of the genome. A well documented relationship exists between DNA methylation, chromatin structure, and gene expression such that methylated genes are generally transcriptionally silent. DNA methylation, which occurs in cancer cells and not in normal cells, suppresses the expression of tumor suppression genes. Inactivation and reversion of gene promoter methylation of tumor suppressor genes with demethylating drugs represents a viable method of treating cancer. Re-expression of silenced tumor suppression genes with demethylating drugs has been reported to result in strong inhibitory effects on cancer cell growth in vitro and in vivo. Hydralazine has shown a demethylating and reactivating effect on various suppressor genes in vitro and in vivo; however the potential use of hydralazine in cancer therapy is limited due to its hypotensive effect. Because the therapeutic levels of hydralazine that are effective in the demethylation and re-expression of tumor suppression genes are similar to those used clinically for hydralazine as an antihypertensive, a concern exists that an unwanted hypotensive effect will occur upon the administration of hydralazine to a patient. An advantage of the present invention is that the hydralazine conjugates can mask the unwanted hypotensive effect in the circulation and safely deliver the hydralazine to the tumor (see: Segura-Pacheco B et al. Clinical Cancer Treatment 9:1596-1603 (2003); Segura-Pacheco B et al. Journal of Translational Medicine 4:32-(2006); Zambrano P et al. BMC Cancer 5:44-(2005) and Martinez et al. US Application 20090042889A1).

Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Scientific publications describing the structural requirements for hydralazine vasodilating activity, bioreductive agents for chemotherapy and radiotherapy in hypoxic tumors, enhancement of chemotherapy with hydralazine, effect of hydralazine on perfusion of tumors, the classification of antineoplastic treatments toward hypoxia and analytical probes for assessing tumor targeting include the following: Druey J and Marxer A Journal of Medicinal and Pharmaceutical Chemistry 1 (1) 1-21 (1959); Patterson L H et al. British Journal of Cancer 82(12):1984-1990 (2000); Brown M J Cancer Research 59:5863-5870 (1999); Harrison L B et al. The Oncologist 7:492-508 (2002); Bremner J C et al. British Journal of Cancer 61(5):717-721 (1990); Brown M J Molecular Medicine Today 6: 157-162 (2000); Airley R E et al. The Pharmacological Journal 264:666-673 (2000); Adams G E et al. International Journal of Radiation Oncology and Biological Physics 16(5):1137-1139 (1989); Horsman M R et al. Experimental Oncology 22:32-37 (2000); Stratfor I J et al. International Journal of Radiation Oncology and Biological Physics 58(2):122-127 (1988); Yamaguchi A Y et al. in CYRIC Annual Report (1990); Dunn J F et al. FEBS Letters 249(2):343-347 (1989); Pusenjak J and Miklavcic D Radiological Oncology 34(1):59-65 (2000); Jarm T et al. Radiological Oncology 35(4):277-291 (2001); Podobnik B et al. In Vivo 15:417-424 (2001); Pusenjak J and Miklavcic D Radiological Oncology 31:291-297 (1997); Similulation Practice and Theory 8:17-24 (2000); Jarm T et al. in Oxygen Transport to Tissue XXIII, edited by D. Wilson et al. Kluwer Academic 25-29 (2003); Jarm T et al. Technology and Health Care 10: 363-380 (2002); Begg A C et al. British Journal of Cancer 83(7):899-905 (2000); Kozin S V and Kozina L V Radiation Research 151(1):79-84 (1999); Belcourt M F et al. Proceedings of the National Avademy of Sciences 93:456-460 (1996); Teicher B A et al. Cancer Research 50, 339-3344 (1990) and Teicher B A et al. Cancer Research 41(1):73-81 (1981); Pouyani T and Prestwich G D Bioconjugate Chemistry 5:370-372 (1994); Murdter T E et al. cancer Research 57:2440-2445 (1997); Luo Y et al. Biomacromolecules 1:208-218 (2000).

The present invention has been described in detail using specific examples to illustrate the preferred embodiments of the invention; however, it will be obvious to those skilled in the art that various modifications thereto can be made without departing from the spirit and scope thereof.

I claim:

1. A pharmaceutical composition comprising a compound having the formula

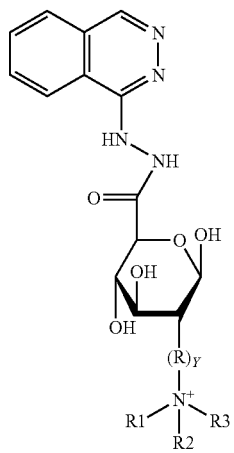

where R is an alkylene or heteroalkylene, Y=0 or 1, $R_1$, $R_2$ and $R_3$ are independently hydrogen, alkyl, aryl, aralkyl or cycloalkyl, and pharmaceutically acceptable salts thereof, in a pharmaceutically acceptable diluent suitable for intravenous administration.

2. The pharmaceutical composition of claim 1 wherein $R_1$, $R_2$ and $R_3$ are hydrogen.

3. The pharmaceutical composition of claim 1 wherein $R_1$, $R_2$ and $R_3$ are alkyl, aryl, aralkyl or cycloalkyl.

4. A method for treating a subject having a solid tumor in need of cancer therapy comprising administering a tumor-targeted conjugate in an amount effective in modulating the inactivation of tumor suppression genes by demethylation of the tumor suppressor genes, said tumor-targeted conjugate having the formula

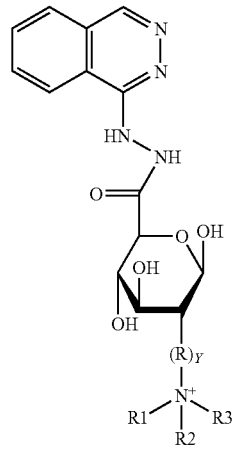

where R is an alkylene or heteroalkylene, Y=0 or 1, $R_1$, $R_2$ and $R_3$ are independently hydrogen, alkyl, aryl, aralkyl or cycloalkyl, and pharmaceutically acceptable salts thereof, in a pharmaceutically acceptable diluent.

* * * * *